US010302583B2

(12) United States Patent
Lu et al.

(10) Patent No.: US 10,302,583 B2
(45) Date of Patent: May 28, 2019

(54) HUMIDITY SENSOR BASED ON SQUARAINE POLYMER, PREPARATION METHOD AND USE THEREOF

(71) Applicant: SOOCHOW UNIVERSITY, Suzhou (CN)

(72) Inventors: Jianmei Lu, Suzhou (CN); Jinghui He, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 254 days.

(21) Appl. No.: 15/608,010

(22) Filed: May 30, 2017

(65) Prior Publication Data
US 2017/0342201 A1 Nov. 30, 2017

(30) Foreign Application Priority Data

May 31, 2016 (CN) .......................... 2016 1 0378962

(51) Int. Cl.
*G01N 27/12* (2006.01)
*C08G 61/12* (2006.01)
*C22C 5/06* (2006.01)

(52) U.S. Cl.
CPC ......... *G01N 27/121* (2013.01); *C08G 61/124* (2013.01); *C22C 5/06* (2013.01); *G01N 27/125* (2013.01); *C08G 2261/3221* (2013.01); *C08G 2261/334* (2013.01); *C08G 2261/94* (2013.01)

(58) Field of Classification Search
CPC .. G01N 27/121; G01N 27/125; G01N 27/605; C08G 61/124; C08G 2261/3221; C08G 2261/334; C08G 2261/94

USPC .................. 73/29.01, 29.02, 335.02
See application file for complete search history.

(56) References Cited

U.S. PATENT DOCUMENTS

| 4,484,172 A * | 11/1984 | Grain .................... G01N 27/121 252/519.1 |
| 2001/0037681 A1* | 11/2001 | Shibue ................. G01N 27/121 73/335.02 |
| 2013/0101767 A1* | 4/2013 | Wei ......................... B01J 47/12 428/35.7 |
| 2015/0185176 A1* | 7/2015 | Koo ..................... G01N 27/223 73/335.04 |

OTHER PUBLICATIONS

Ajayaghosh, "Chemistry of Squaraine-Derived Materials: Near-IR Dyes, Low Band Gap Systems, and Cation Sensors" (Year: 2005).*

* cited by examiner

*Primary Examiner* — Benjamin R Schmitt
(74) *Attorney, Agent, or Firm* — SZDC Law P.C.

(57) ABSTRACT

The invention discloses a humidity sensor based on squaraine polymer and the preparation method and use thereof. Specifically, the humidity sensor disclosed by the invention comprises a coating material and an interdigital electrode, wherein the coating material is a squaraine polymer as shown in formula I, n is an integer of 40-50, the coating material is brushed on the interdigital electrode, and the thickness is 100-400 microns. The humidity sensor disclosed by the invention has the advantages that the preparation is convenient, and the operation is simple; the response time is short, and the response for humidity change is higher than that of common metallic oxides; the recovery time is short, and the device performance is stable; the humidity hysteresis of the device is high under high humidity environment.

9 Claims, 3 Drawing Sheets

HUMIDITY SENSOR BASED ON SQUARAINE POLYMER, PREPARATION METHOD AND USE THEREOF

This application claims priority to Chinese Patent Application No. 201610378962.X, filed on May 31, 2016, which is incorporated by reference for all purposes as if fully set forth herein.

TECHNICAL FIELD

The present invention belongs to the technical field of organic semiconductor materials, particularly relates to a humidity sensor based on squaraine polymer, the preparation method and its use in air humidity detecting.

BACKGROUND TECHNIQUE

With the development of science and technology, the requirements for environmental humidity are becoming higher in many fields, for example, the environmental humidity should be effectively monitored in aerospace industry, agriculture, precision machinery and laboratory. At present, researching of humidity sensor is a hot direction of the researching of many sensor fields. The common humidity sensors are usually based on metal oxide materials. Although the stability of such humidity sensor is good, but the selectivity is poor and the preparation process is relatively complex, so that it is not suitable for large-scale application. In order to meet the requirements of the market for low cost, practical and easy preparation, a new type of humidity sensor is urgently needed.

SUMMARY OF THE INVENTION

According to such situation, the present invention adopts a squaraine polymer PMPS (The structure is shown as follows, wherein n is an integer of 40-50) to prepare humidity sensitive sensor, and to detect the air of different humidity by observing the complex impedance changes of the sensor under different humidity. In the present invention, the impedance variation of the humidity sensor is tested at different frequencies, to show that the maximum complex impedance appears at 100 Hz. In the present invention, the recovery property of the device is also tested. The device is put in a humidity atmosphere with relative humidity (RH) of 11%, the impedance is detected as about $7 \times 10^8$, then put in a humidity atmosphere of 95% to detect as about $1 \times 10^4$. In the present invention, the adsorption and desorption performance is also tested in a humidity atmosphere with relative humidity from 11% to 95%.

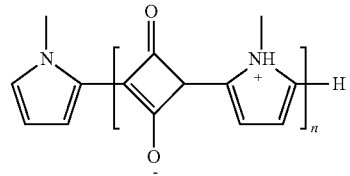

In particularly, the present invention adopts the following technical solutions.

A humidity sensor based on squaraine polymer, comprises a coating material and an interdigital electrode, said coating material is a squaraine polymer as shown in formula (I), wherein n is an integer of 40-50, the coating material is brushed on said interdigital electrode, and the thickness is 100-400 microns.

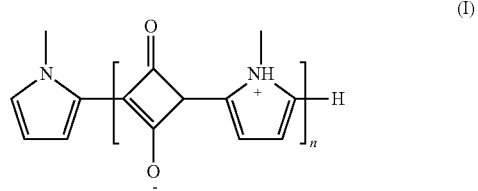

Preferably, in said humidity sensor based on squaraine polymer, said interdigital electrode has a base made by alumina ($Al_2O_3$) with a thickness of 1-2 mm, on which a layer of silver palladium (Ag—Pd) alloy with a thickness of 100-200 nm is set.

Preferably, in said humidity sensor based on squaraine polymer, said interdigital electrode has an interdigital width of 200-300 μm, and an interdigital distance of 100-200 μm.

A preparation method of a humidity sensor based on squaraine polymer, comprising the following steps:

(1) cleaning a substrate and fixing an interdigital electrode on said substrate;

(2) dissolving a squaraine polymer as shown in formula (I) in a solvent according to weight ratio of squaraine polymer:solvent=4:1, using ultrasound to disperse it evenly, to obtain a squaraine polymer solution;

(3) painting said squaraine polymer solution on the interdigital electrode, after the solvent evaporates at room temperature, drying at temperature of 60-80° C. for 1-2 hours, to obtain the humidity sensor based on squaraine polymer.

Preferably, in the step (1), said substrate is selected from any one of a glass substrate, a PE substrate and an iron sheet substrate, more preferably a glass substrate.

Preferably, in the step (1), said fixing is achieved by using a double tape as a spacer.

Preferably, in the step (2), said solvent is selected from any one of ethanol, dichloromethane and ethyl acetate, more preferably ethanol.

Preferably, in the step (3), said drying is completed through vacuum drying oven.

Preferably, in the step (3), the drying temperature is 60° C., the drying time is 1 hour.

The use of said humidity sensor based on squaraine polymer in air humidity detecting.

Compared with the prior art, the present invention adopting the above technical solution has the following advantages:

(1) The device is convenient to prepare and easy to operate;

(2) The response time is shorter, and the response for humidity change is higher than that of common metallic oxides;

(3) The recovery time is short and the performance of the device is stable;

(4) The device has strong humidity hysteresis in high humidity environment.

DETAILED DESCRIPTION

The technical solution of the present invention will be further described hereinafter with reference to the accompanying figures and examples. Unless otherwise indicated, reagents, materials, instruments, etc., used in the examples below may be obtained commercially.

Example 1: Synthesis of PMPS and Preparation of the Sensor (1) Synthesis of PMPS Molecule:

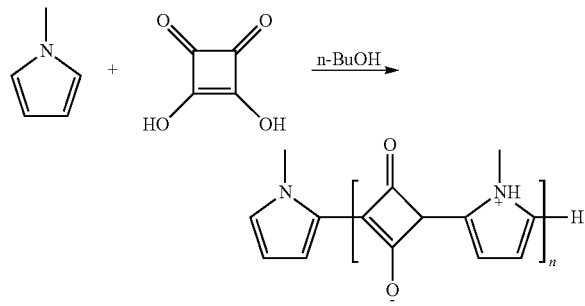

Preparing 1-methylpyrrolidine (1.62 g, 20 mmol) and squaric acid (2.32 g, 20 mmol), and putting in 1-butanol (150 mL), heating and refluxing for 18 h. After the reaction, filtering to get the solid and put in a Soxhlet extractor, washing with ethyl acetate for 4 h, drying to obtain PMPS (3 g; yield 75%; element analysis: theoretical values: N: 8.58, C: 66.25, H: 5.56; actual values: N: 8.23, C: 65.84, H: 5.48; the molecular weight determined by GPC is 6500-8200, and the polymerization degree n calculated is 40-50), the SEM microstructure is shown in FIG. 1, and the IR spectrum is shown in FIG. 2.

Figure 1:
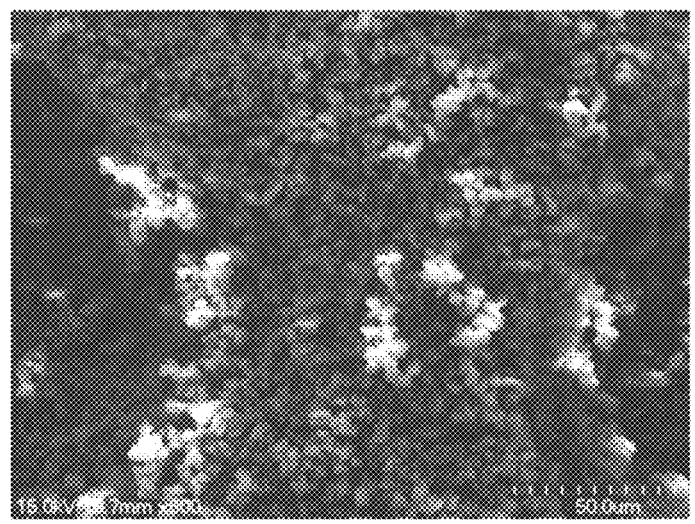
FIG. 1 shows the SEM of the squaraine polymer PMPS.

As can be seen from FIG. 1, PMPS is a relatively uniform spherical particle with more porous pores, which facilitates the preparation of sensors for detecting environmental humidity.

Figure 2:
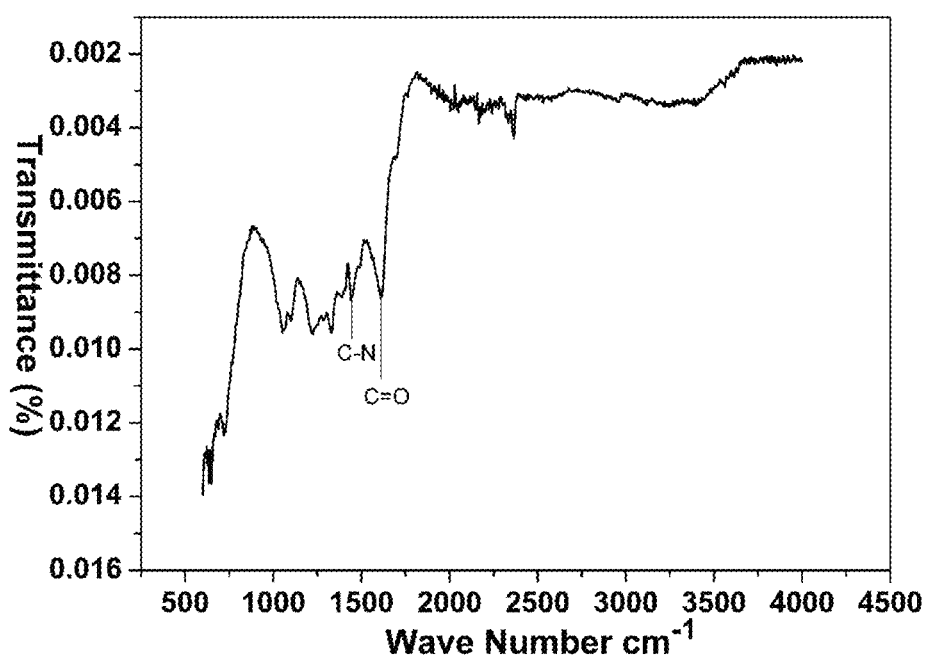
FIG. 2 shows the IR spectra of the squaraine polymer PMPS.

As shown in FIG. 2, after polymerization, the characteristic peaks in hydroxyl acid disappeared and C=O peaks retained, the peak position of the characteristic peaks of C—N bond has a certain shift due to the change of the charge density, showing that the PMPS molecular polymer is prepared successfully.

(2) Preparation of the Sensor:

(a) Cleaning the glass substrate, fixing the interdigital electrode on the substrate using a double tape as a spacer; the interdigital electrode has a base made by $Al_2O_3$ (1 mm), on which a Ag—Pd alloy electrode (100 nm) is set, the interdigital width is 0.2 mm, and an interdigital distance is 0.2 mm.

Figure 3:
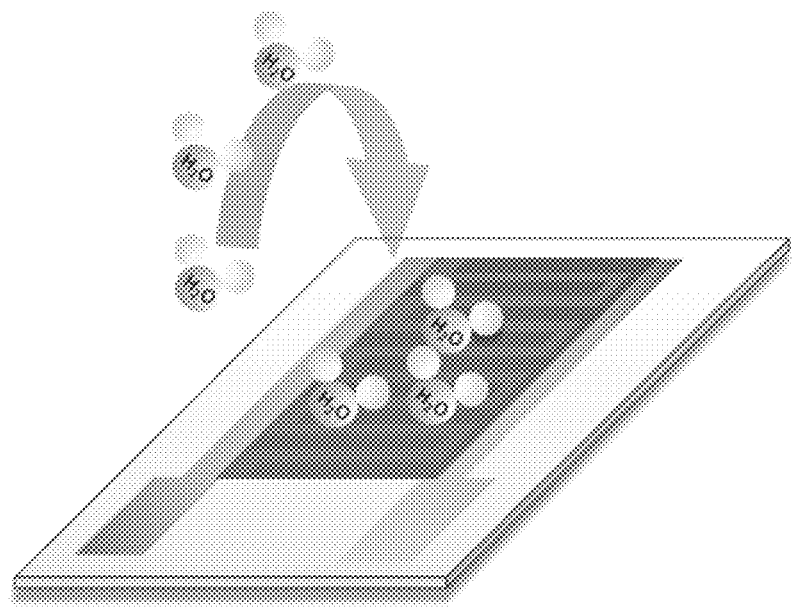
FIG. 3 shows the structure of the humidity sensor based on squaraine polymer.

(b) dissolving PMPS (4 mg) in ethanol (2 g), using ultrasound to disperse it evenly, to obtain an ethanol solution of squaraine polymer;

(c) painting the ethanol solution of squaraine polymer on the interdigital electrode, after the ethanol evaporates at room temperature, drying at temperature of 60° C. for 1 hour, to obtain the humidity sensor based on squaraine polymer, the structure is shown in FIG. 3, wherein the thickness of the PMPS coating is 300 μm.

Example 2: The Impedance of the Humidity Sensor Tested at Different Frequencies

Figure 4:
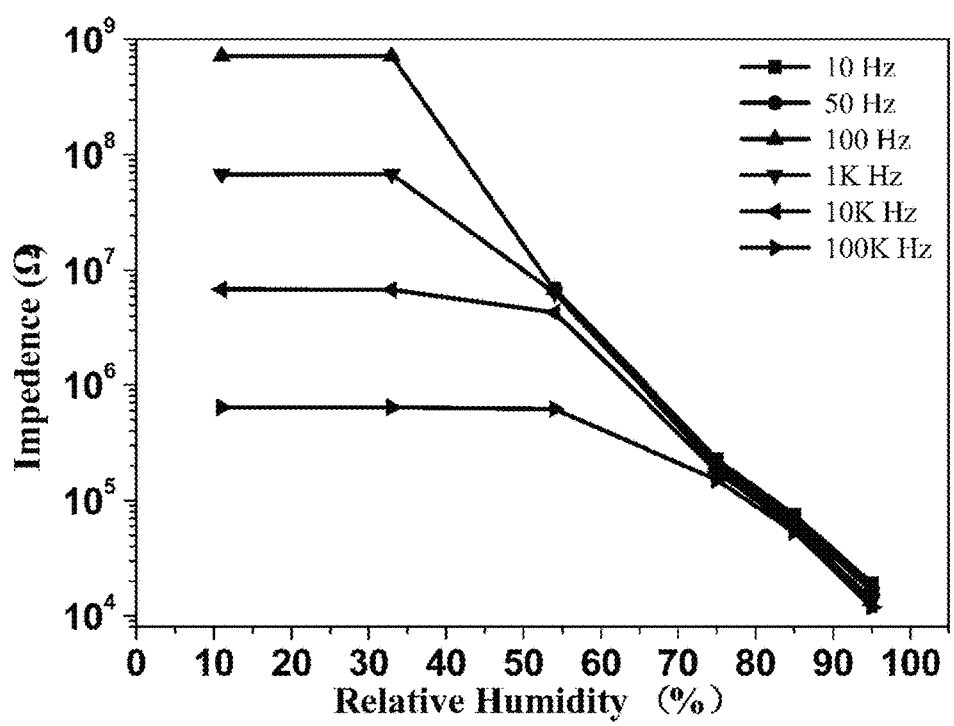
FIG. 4 shows the effect picture of the device's impedance response to humidity under different frequencies.

Put the device prepared in Example 1 in the testing machine, adjusting the frequency between 10 kHz-100 kHz, detecting the impedance changes of the device at different relative humidity of 11%, 33%, 54%, 75%, 85% and 95%, the results are shown in FIG. 4.

As shown in FIG. 4, for different concentrations of humidity atmosphere, the humidity sensor based on squaraine polymer has different impedance changes in different frequency, which can be seen at 100 Hz, the device has best linear relationship and strongest response.

Example 3: The Recovery Property of the Humidity Sensor at the RH from 11% to 95%

At the frequency of 100 Hz, the device is fixed with the condition of 11% relative humidity, after impedance staying stable, relative humidity is changed to 95%, after impedance staying stable again, return to 11%. Repeat the cycle, the result is shown in FIG. 5.

Figure 5:
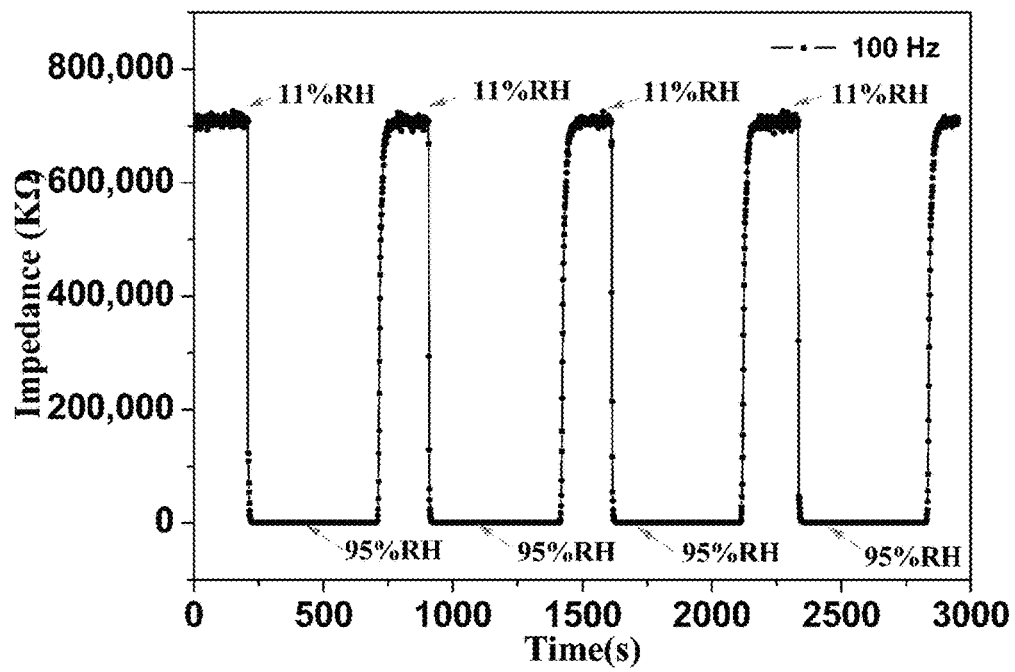
FIG. 5 shows the effect picture of the device's recovery property in the relative humidity between 11% and 95%.

As can be seen from FIG. 5, the stability of the device is excellent, the response time is as short as 3 s, the recovery time is as short as 16 s, it can be found that the device does not only have good stability, but also have short response time and recovery time.

Figure 6:
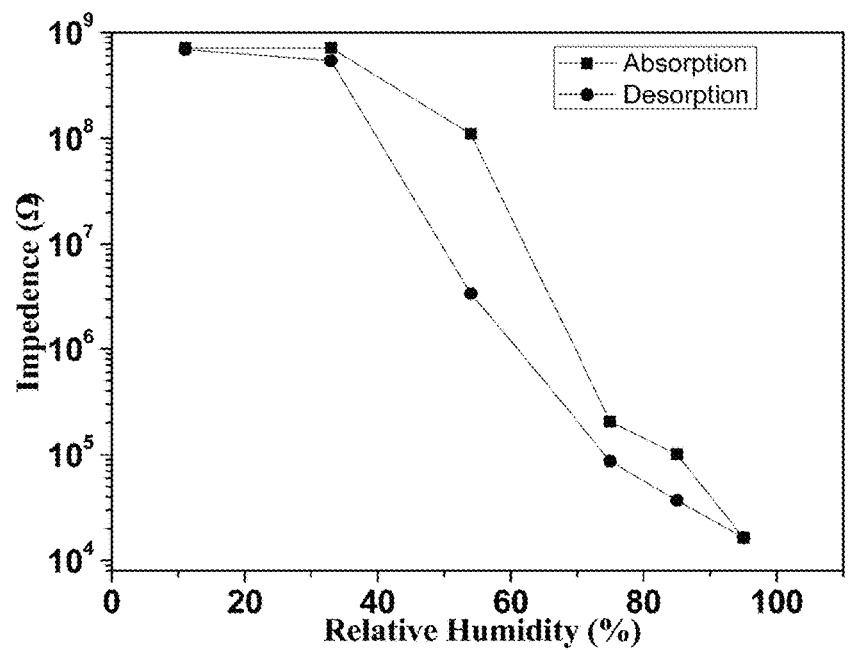
FIG. 6 shows the device's absorption and desorption curves at different humidity.

Example 4: The Measurement Experiment of the Adsorption/Desorption Performance of the Humidity Sensor Based on Squaraine Polymer The adsorption/desorption performance of the sensor is measured at 100 Hz with different relative humidity atmosphere, the result is shown in FIG. 6. It can be seen that the device has good adsorption/desorption performance.

In summary, this invention provides a thin film humidity sensor with simple structure based on squaraine polymer, to realize the detection of different air humidity. It has fast response time and recovery time. It solves the problem of lack of humidity sensor based on organic polymer at present time. Therefore, the humidity sensor based on polymer squaraine has great value for the controlling of the environmental humidity in the future.

The invention claimed is:

1. A humidity sensor based on squaraine polymer, which comprising a coating material and an interdigital electrode, said coating material is a squaraine polymer as shown in formula (I), wherein n is an integer of 40-50, the coating material is brushed on said interdigital electrode, and the thickness of the coating material is 100-400 microns;

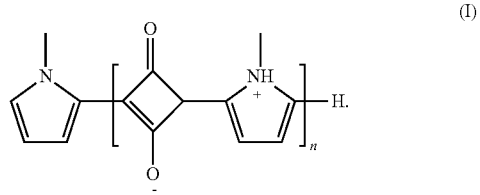

(I)

2. The humidity sensor based on squaraine polymer according to claim 1, wherein:
said interdigital electrode has a base made by alumina with a thickness of 1-2 mm, on which a layer of silver palladium alloy with a thickness of 100-200 nm is set.

3. The humidity sensor based on squaraine polymer according to claim 1, wherein:
said interdigital electrode has an interdigital width of 200-300 μm, and an interdigital distance of 100-200 μm.

4. A preparation method of a humidity sensor based on squaraine polymer according to claim 1, comprising the following steps:
(1) cleaning a substrate and fixing an interdigital electrode on said substrate;
(2) dissolving a squaraine polymer as shown in formula (I) in a solvent according to weight ratio of squaraine polymer:solvent=4:1, using ultrasound to disperse it evenly, to obtain a squarain polymer solution;
(3) painting said squarain polymer solution on the interdigital electrode, after the solvent evaporates at room temperature, drying at temperature of 60-80° C. for 1-2 hours, to obtain the humidity sensor based on squaraine polymer.

5. The preparation method according to claim 4, wherein:
in the step (1), said substrate is selected from any one of a glass substrate, a PE substrate and an iron sheet substrate.

6. The preparation method according to claim 4, wherein:
in the step (1), said fixing is achieved by using a double tape as a spacer.

7. The preparation method according to claim 4, wherein:
in the step (2), said solvent is selected from any one of ethanol, dichloromethane and ethyl acetate.

8. The preparation method according to claim 4, wherein:
in the step (3), said drying is completed through vacuum drying oven.

9. The preparation method according to claim 4, wherein:
in the step (3), the drying temperature is 60° C., the drying time is 1 hour.

\* \* \* \* \*